United States Patent [19]

Rivier et al.

[11] 4,444,759
[45] Apr. 24, 1984

[54] GNRH ANTAGONISTS II

[75] Inventors: Jean E. F. Rivier; Wylie W. Vale, Jr., both of La Jolla, Calif.

[73] Assignee: The Salk Institute for Biological Studies, San Diego, Calif.

[21] Appl. No.: 402,117

[22] Filed: Jul. 26, 1982

[51] Int. Cl.$^3$ .................... C07C 103/52; A61K 37/02
[52] U.S. Cl. ............................ 424/177; 260/112.5 LH
[58] Field of Search ............................. 260/112.5 LH

[56] References Cited

U.S. PATENT DOCUMENTS

| | | | |
|---|---|---|---|
| 4,072,668 | 2/1978 | Amoss et al. | 260/112.5 LH |
| 4,118,483 | 10/1978 | König et al. | 260/112.5 LH |
| 4,215,038 | 7/1980 | Rivier et al. | 260/112.5 LH |
| 4,253,997 | 3/1981 | Sarantakis | 260/112.5 LH |
| 4,261,887 | 4/1981 | Amoss et al. | 260/112.5 LH |
| 4,292,313 | 9/1981 | Vale, Jr. et al. | 260/112.5 LH |
| 4,307,083 | 12/1981 | Rivier et al. | 260/112.5 LH |
| 4,341,767 | 7/1982 | Nestor et al. | 260/112.5 LH |

FOREIGN PATENT DOCUMENTS 2053229 2/1981 United Kingdom .

OTHER PUBLICATIONS

C. W. Beattie, et al., J. of Med. Chem. (1975) vol. 18, No. 12, pp. 1247–1250.
Peptide Antagonists of LH–RH: Large Increases in Antivulatory Activities Produced by Basic D-Amino Acids in the 6-Position, *Endocrinology* pp. 1445–1447.

*Primary Examiner*—Delbert R. Phillips
*Assistant Examiner*—F. T. Moezie
*Attorney, Agent, or Firm*—Fitch, Even, Tabin & Flannery

[57] ABSTRACT

Peptides which inhibit the secretion of gonadotropins by the pituitary gland and inhibit the release of steroids by the gonads. Administration of an effective amount prevents ovulation of female mammalian eggs and/or the release of steroids by the gondads. The peptides have the structure.

$X$-$\beta$-D-2NAL-$R_2$-D-Trp-Ser-$R_5$-$R_6$-$R_7$-Arg-Pro-$R_{10}$ wherein X is hydrogen or an acyl group having 7 or less carbon atoms; $R_2$ is Cl-D-Phe, F-D-Phe, $NO_2$-D-Phe, $Cl_2$-D-Phe or Br-D-Phe; $R_5$ is Tyr or Cl-Phe; $R_6$ is 4-$NH_2$-D-Phe or D-Arg; $R_7$ is Leu or N$\alpha$Me-Leu; and $R_{10}$ is Gly-$NH_2$, $NHCH_2CH_3$ or D-Ala-$NH_2$.

20 Claims, No Drawings

GNRH ANTAGONISTS II

This invention was made with Government support under Contract No. NO1-HD-O-2836 and/or Grant HD13527 awarded by DHHS(NIH). The Government has certain rights in this invention.

The present invention relates to peptides which inhibit the release of gonadotropins by the pituitary gland in mammalians, including humans, and to methods of preventing ovulation and/or inhibiting the release of steriods. More particularly, the present invention is directed to peptides which inhibit gonadal function and the release of the steroidal hormones, progesterone and testosterone.

BACKGROUND OF THE INVENTION

The pituitary gland is attached by a stalk to the region in the base of the brain known as the hypothalamus. In particular, follicle stimulating hormone (FSH) and luteinizing hormone (LH), sometimes referred to as gonadotropins or gonadotropic hormones, are released by the pituitary gland. These hormones, in combination, regulate the functioning of the gonads to produce testosterone in the testes and progesterone and estrogen in the ovaries, and also regulate the production and maturation of gametes.

The release of a hormone by the anterior lobe of the pituitary gland usually requires a prior release of another class of hormones produced by the hypothalamus. One of the hypothalamic hormones acts as a factor that triggers the release of the gonadotropic hormones, particularly LH, and this hormone is referred to herein as GnRH although it has also been referred to as LH-RH and as LRF. GnRH has been isolated and characterized as a decapeptide having the following structure:

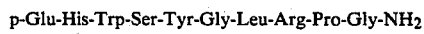

Peptides are compounds which contain two or more amino acids in which the carboxyl group of one acid is linked to the amino group of the other acid. The formula for GnRH, as represented above, is in accordance with conventional representation of peptides where the amino group appears to the left and the carboxyl group to the right. The position of the amino acid residue is identified by numbering the amino acid residues from left to right. In the case of GnRH, the hydroxyl portion of the carboxyl group of glycine has been replaced with an amino group (NH$_2$). The abbreviations for the individual amino acid residues above are conventional and are based on the trivial name of the amino acid, e.g. p-Glu is pyroglutamic acid, His is histidine, Trp is tryptophan, Ser is serine, Tyr is tyrosine, Gly is glycine, Leu is Leucine, Arg is arginine, Pro is proline, Phe is phenylalanine and Ala is alanine. These amino acids together with valine, isoleucine, threonine, lysine, aspartic acid, asparagine, glutamine, cysteine, methionine, phenylalanine, and proline are generally considered to be the common, naturally occurring or protein-derived amino acids. Except for glycine, amino acids of the peptides of the invention are of the L-configuration unless noted otherwise.

It is well known that the substitution of D-amino acids for Gly in the 6-position of the GnRH decapeptide provides a peptide material having from about 1 to 35 times greater potency than does GnRH to effect the release of LH and other gonadotropins by the pituitary gland of mammalians. It is taught by K. U. Prasad et al. *J. Med. Chem.*, Vol. 19, 492 (1976) that greater potency is also achieved by the substitution in the 3-position of 3-(1-naphthyl) Ala. The releasing effect is obtained when the GnRH analog is administered to a mammalian intravenously, subcutaneously, intramuscularly, orally, intranasally or intravaginally.

It is also known that substitution of various amino acids for His (or the deletion of His) at the 2-position of the GnRH decapeptide produces analogs having an inhibitory effect on the release of LH and other gonadotropins by the pituitary gland of mammalians.

There are reasons for desiring to prevent ovulation in female mammalians, and the administration of GnRH analogs that are antagonistic to the normal function of GnRH have been used to prevent ovulation. For this reason, analogs of GnRH which are antagonistic to GnRH are being investigated for their potential use as a contraceptive or for regulating conception periods. Such antagonists have also been found useful to regulate the secretion of gonadotropins in male mammals and can be employed as male contraceptives. It is desired to provide peptides which are strongly antagonistic to endogenous GnRH and which prevent secretion of LH and the release of steriods by the gonads of mammals.

SUMMARY OF THE INVENTION

The present invention provides peptides which inhibit the release of gonadotropins in mammalians, including humans, and also provides methods for inhibiting the release of steroids by the gonads of male and female mammalians. The improved GnRH analogs are antagonistic to GnRH and have an inhibitory effect on the reproduction processes of mammalians. These analogs may be used to inhibit the production of gonadotropins and sex hormones under various circumstances including precocious puberty, hormone dependent neoplasia, dysmenorrhea and endometriosis.

Generally, in accordance with the present invention, peptides have been synthesized which strongly inhibit the secretion of gonadotropins by the pituitary gland of mammalians, including humans, and/or inhibit the release of steroids by the gonads. These peptides are analogs of GnRH wherein there is a 1-position substitution in the form of β-(2-naphthyl) D-alanine (hereinafter, β-D-2NAL), a 3-position substitution in the form of D-Trp, a 6-position substitution and a substituent is also present in the 2-position. The 1-position substituent may be modified so that its alpha amino group contains an acyl group, such as formyl, acetyl, acrylyl, vinylacetyl or benzoyl, with acetyl (Ac) and acrylyl (Acr) being preferred. Modified D-Phe is preferably present in the 2-position and provides increased antagonistic activity as a result of the specific modifications present in the benzene ring. Single substitutions for hydrogen are preferably made in the para- and 4-position, and the substitutions are selected from chloro, fluoro, bromo, and nitro, with chloro and fluoro being preferred. Double substitutions are preferably made in the 3- and 4-positions, e.g. 3,4-Cl-D-Phe. 4-NH$_2$-D-Phe or D-Arg is present in the 6-position. The substitutions in the 5-,7- and 10-positions are optional. When Cl-Phe is inserted in the 5-position, the Cl is preferably present in the ortho or 2-position.

Because these peptides are highly potent to inhibit release of LH, they are often referred to as GnRH antagonists. The peptides inhibit ovulation of female mammals when administered at very low levels at proestrous and are also effective to cause resorption of fertilized eggs if administered shortly after conception. These peptides are also effective for the contraceptive treatment of male mammals.

DETAILED DESCRIPTION OF THE PREFERRED EMBODIMENTS

More specifically, the peptides of the present invention are represented by the following formula:

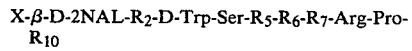

wherein X is hydrogen or an acyl group having 7 or less carbon atoms; $R_2$ is Cl-D-Phe, F-D-Phe, $NO_2$-D-Phe, $Cl_2$-D-Phe or Br-D-Phe; $R_5$ is Tyr or Cl-Phe; $R_6$ is D-Arg or 4-$NH_2$-D-Phe; $R_7$ is Leu or N Me-Leu; and $R_{10}$ is Gly-$NH_2$, $NHCH_2CH_3$ or D-Ala-$NH_2$.

By β-D-NAL is meant the D-isomer of alanine which is substituted by naphthyl on the β-carbon atom, which may also be designated 3-D-NAL. Preferably β-D-2NAL is employed which means that the β-carbon atom is attached to naphthalene at the 2-position on the ring structure.

The peptides of the present invention can be synthesized by classical solution synthesis or by a solid phase technique using a chloromethylated resin, a methylbenzhydrylamine resin (MBHA) or a benzhydrylamine (BHA) resin. The solid phase synthesis is conducted in a manner to stepwise add the amino acids in the chain in the manner set forth in detail in the U.S. Pat. No. 4,211,693. Side-chain protecting groups, as are well known in the art, are preferably added to Ser, Tyr, Arg and His, and may optionally be added to Trp, before these amino acids are coupled to the chain being built upon the resin. Such a method provides the fully protected intermediate peptidoresin.

The intermediates of the invention may be represented as:

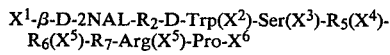

wherein: $X^1$ is an α-amino protecting group of the type known to be useful in the art in the stepwise synthesis of polypeptides and when X in the desired peptide composition is a particular acyl group, that group may be used as the protecting group. Among the classes of α-amino protecting groups covered by $X^1$ are (1) acyl-type protecting groups, such as formyl (For), trifluoroacetyl, phthalyl, p-toluenesulfonyl (Tos), benzoyl (Bz), benzensulfonyl, o-nitrophenylsulfenyl (Nps), tritylsulfenyl, o-nitrophenoxyacetyl, acrylyl (Acr), chloroacetyl, acetyl (Ac) and γ-chlorobutyryl; (2) aromatic urethan-type protecting groups, e.g., benzyloxycarbonyl (Z) and substituted benzyloxycarbonyl, such as p-chloro-benzyloxycarbonyl, p-nitrobenzyloxycarbonyl, p-bromobenzyloxycarbonyl and p-nethoxybenzyloxycarbonyl; (3) aliphatic urethan protecting groups, such as tertbutyloxycarbonyl (Boc), diisopropylmethoxycarbonyl, isopropyloxycarbonyl, ethoxycarbonyl and allyloxycarbonyl; (4) cycloalkyl urethan-type protecting groups, such as cyclopentyloxycarbonyl, adamantyloxycarbonyl and cyclohexyloxycarbonyl; (5) thiourethan-type protecting groups, such as phenylthiocarbonyl; (6) alkyl-type protecting groups, such as allyl (Aly), triphenylmethyl(trityl) and benzyl (Bzl); (7) trialkylsilane groups, such as trimethylsilane. The preferred α-amino protecting group is Boc when X is hydrogen.

$X^2$ is hydrogen or a protecting group for the indole nitrogen, such as formyl or benzyl; however in many syntheses there is no need to protect Trp.

$X^3$ is hydrogen or a protecting group for the alcoholic hydroxyl group of Ser and is selected from the group consisting of acetyl, benzoyl, tetrahydropyranyl, tert-butyl, trityl, benzyl and 2,6-dichlorobenzyl. Benzyl is preferred.

$X^4$ is hydrogen or a protecting group for the phenolic hydroxyl group of Tyr selected from the group consisting of tetrahydropyranyl, tert-butyl, trityl, benzyl, benzyloxycarbonyl, 4-bromobenzyloxycarbonyl and 2,6-dichlorobenzyl. 2,6-dichlorobenzyl is preferred.

$X^5$ is a protecting group for the nitrogen atoms of Arg and is selected from the group consisting of nitro, Tos, benzyloxycarbonyl, adamantyloxycarbonyl, and Boc; alternatively $X^5$ may be hydrogen, which means there are no protecting groups on the side chain nitrogen atoms of arginine. Tos is preferred.

$X^6$ is selected from the group consisting of Gly-O-$CH_2$-[resin support]; O-$CH_2$-[resin support]; D-Ala-O-$CH_2$-[resin support]; Gly-NH-[resin support]; D-Ala-NH-[resin support]; and OH, ester, amide and hydrazide of either Gly or D-Ala or attached directly to Pro.

The criterion for selecting side chain protecting groups for $X^2$-$X^5$ is that the protecting group must be stable to the reagent under the reaction conditions selected for removing the α-amino protecting group at each step of the synthesis. The protecting group must not be split off under coupling conditions, and the protecting groups must be removable upon completion of the synthesis of the desired amino acid sequence under reaction conditions that will not alter the peptide chain.

When the $X^6$ group is Gly-O-$CH_2$-[resin support], D-Ala-O-$CH_2$-[resin support] or O-$CH_2$-[resin support], the ester moiety of one of the many functional groups of the polystyrene resin support is being represented. When the $X^6$ group is Gly-NH-[resin support] or D-Ala-NH-[resin support], an amide bond connects Gly or D-Ala to BHA resin or to a MBHA resin.

When X is, for example, in the final formula, it may be possible to employ it as the $X^1$ protecting group for the α-amino group of D-NAL by adding it before the coupling of this last amino acid to the peptide chain. However, a reaction is preferably carried out with the peptide on the resin (after deblocking the α-amino group while the side-chain groups remain protected), e.g., by reacting with acetic acid in the presence of dicyclohexyl carbodiimide (DCC) or preferably with acetic anhydride or by another suitable reaction as known in the art.

The fully protected peptide can be cleaved from a chloromethylated resin support by ammonolysis, as is well known in the art, to yield the fully protected amide intermediate. Deprotection of the peptide, as well as cleavage of the peptide from a benzhydrylamine resin, can take place at 0° C. with hydrofluoric acid (HF). Anisole is preferably added to the peptide prior to treatment with HF. After the removal of HF, under vacuum, the cleaved, deprotected peptide is conveniently treated with ether, decanted, taken-up in dilute acetic acid and lyophilized.

Purification of the peptide is effected by ion exchange chromatography on a CMC column, followed by partition chromatography using the elution system: n-butanol; 0.1 N acetic acid (1:1 volume ratio) on a column packed with Sephadex G-25, or by using HPLC, as known in the art.

The peptides of the invention are effective at levels of less than 100 micrograms per kilogram of body weight, when administered at about noon on the day of proestrous, to prevent ovulation in female rats. For prolonged suppression of ovulation, it may be necessary to use dosage levels in the range of from about 0.1 to about 2.5 milligrams per kilogram of body weight. These antagonists are also effective as contraceptives when administered to male mammals on a regular basis. Since these compounds will reduce testosterone levels (an undesired consequence in the normal, sexually active male), it may be reasonable to administer replacement dosages of testosterone along with the GnRH antagonist. These antagonists can also be used to regulate the production of gonadotropins and sex steroids for other purposes as indicated hereinbefore.

EXAMPLE

Peptides as indicated in Table I having the formula

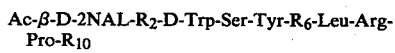

Ac-β-D-2NAL-$R_2$-D-Trp-Ser-Tyr-$R_6$-Leu-Arg-Pro-$R_{10}$ are prepared by the solid phase procedure referred to above.

TABLE I

|   | $R_2$ | $R_6$ | $R_{10}$ |
|---|---|---|---|
| 1 | 4-F—D-Phe | D-Arg | Gly—$NH_2$ |
| 2 | " | 4-$NH_2$—D-Phe | " |
| 3 | 4-Cl—D-Phe | D-Arg | " |
| 4 | 4-Cl—D-Phe | " | NH$CH_2CH_3$ |
| 5 | 4-$NO_2$—D-Phe | " | " |
| 6 | 4-Br—D-Phe | " | " |
| 7 | 4-F—D-Phe | " | D-Ala—$NH_2$ |
| 8 | " | " | Gly—$NH_2$ ($N^\alpha$MeLeu$^7$) |
| 9 | " | " | Gly—$NH_2$ (2-Cl—Phe$^5$) |
| 10 | " | " | Gly—$OCH_3$ |
| 11 | " | " | Gly—$NHNH_2$ |

For purposes of an example, a representative solid phase synthesis of Peptide No. 1 above, which is referred to as [Ac-β-D-2NAL$^1$, 4-F-D-Phe$^2$,D-Trp$^3$, D-Arg$^6$]-GnRH is set forth hereinafter. This peptide has the following formula:

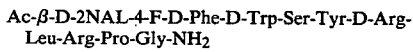

Ac-β-D-2NAL-4-F-D-Phe-D-Trp-Ser-Tyr-D-Arg-Leu-Arg-Pro-Gly-$NH_2$

A BHA resin is used, and Boc-protected Gly is coupled to the resin over a 2-hour period in $CH_2Cl_2$ using a 3-fold excess of Boc derivative and DCC as an activating reagent. The glycine residue attaches to the BHA residue by an amide bond.

Following the coupling of each amino acid residue, washing, deblocking and coupling of the next amino acid residue is carried out in accordance with the following schedule using an automated machine and beginning with about 5 grams of resin:

| STEP | REAGENTS AND OPERATIONS | MIX TIMES MIN. |
|---|---|---|
| 1 | $CH_2Cl_2$ wash-80 ml. (2 times) | 3 |
| 2 | Methanol(MeOH) wash-30 ml. (2 times) | 3 |
| 3 | $CH_2Cl_2$ wash-80 ml. (3 times) | 3 |
| 4 | 50 percent TFA plus 5 percent 1,2-ethanedithiol in $CH_2Cl_2$-70 ml. (2 times) | 10 |
| 5 | $CH_2Cl_2$ wash-80 ml. (2 times) | 3 |
| 6 | TEA 12.5 percent in $CH_2Cl_2$-70 ml. (2 times) | 5 |
| 7 | MeOH wash-40 ml. (2 times) | 2 |
| 8 | $CH_2Cl_2$ wash-80 ml. (3 times) | 3 |
| 9 | Boc-amino acid (10 mmoles) in 30 ml. of either DMF or $CH_2Cl_2$, depending upon the Solubility of the particular protected amino acid, (1 time) plus DCC (10 mmoles) in $CH_2Cl_2$ | 30–300 |
| 10 | MeOH wash-40 ml. (2 times) | 3 |
| 11 | TEA 12.5 percent in $CH_2Cl_2$-70 ml. (1 time) | 3 |
| 12 | MeOH wash-30 ml. (2 times) | 3 |
| 13 | $CH_2Cl_2$ wash-80 ml. (2 times) | 3 |

After step 13, an aliquot is taken for a ninhydrin test: if the test is negative, go back to step 1 for coupling of the next amino acid; if the test is positive or slightly positive, go back and repeat steps 9 through 13.

The above schedule is used for coupling of each of the amino acids of the peptide of the invention after the first amino acid has been attached. NαBoc protection is used for each of the remaining amino acids throughout the synthesis. NαBoc-β-D-2NAL is prepared by a method known in the art, e.g. as described in detail in U.S. Pat. No. 4,234,571, issued Nov. 18, 1980. The side chain of Arg is protected with Tos. OBzl is used as a side chain protecting group for the hydroxyl group of Ser, and 2-6 dichlorobenzyl is used as the side chain protecting group for the hydroxyl group of Tyr. Trp is left unprotected. NαBoc-β-D-2NAL is introduced as the final amino acid. Boc-Arg(Tos) and Boc-D-Trp, which have low solubility in $CH_2Cl_2$, are coupled using DMF:$CH_2Cl_2$ mixtures.

After deblocking the γ-amino group at the N-terminal, acetylation is achieved using a large excess of acetic anhydride in dichloromethane. The cleaveage of the peptide from the resin and complete deprotection of the side chains takes place very readily at 0° C. with HF. Anisole is added as a scavenger prior to HF treatment. After the removal of HF under vacuum, the resin is extracted with 50% acetic acid, and the washings are lyophilized to provide a crude peptide powder.

Purification of the peptide is then effected by ion exchange chromatography on CMC (Whatman CM 32, using a gradient of 0.05 to 0.3 M $NH_4OAc$ in 50/50 methanol/water) followed by partition chromatography in a gel filtration column using the elution system: n-Butanol; 0.1 N Acetic acid (1:1-volume ratio).

The peptide is judged to be homogeneous using thin layer chromatography and several different solvent systems, as well as by using reversed-phase high pressure liquid chromatography and an aqueous triethylammonium phosphate solution plus acetonitrile. Amino acid analysis of the resultant, purified peptide is consistent with the formula for the prepared structure, showing substantially integer-values for each amino acid in the chain. The optical rotation is measured on a photoelectric polarimeter as $[\alpha]_D^{22} = -29° \pm 1 (c=1, 50\%$ acetic acid).

The peptide is assayed in vitro and in vivo. The in vitro test is made using dissociated rat pituitary cells maintained in culture for 4 days prior to the assay. The levels of LH mediated in response to the application of peptides is assayed by specific radioimmunoassay for rat LH. Control dishes of cells only receive a measure which is 3 nanomolar in GnRH; experimental dishes receive a measure 3 nanomolar in GnRH plus a measure having either the present standard antagonist (for comparison purposes) i.e. [Ac-dehydro Pro$^1$, 4-F-D-Phe$^2$, D-Trp$^{3,6}$]-GnRH or the test peptide in concentrations ranging from 0.01 to 10 nanomolar. The amount of LH secreted in the samples treated only with GnRH is compared with that secreted by the samples treated with the peptide plus GnRH.

The ability of the test peptide to reduce the amount of LH released by 3 nanomolar GnRH is compared to that of the present standard peptide. The results are calculated using 3-5 doses of each of the peptides by the statistical program BIOPROG (provided by D. Rodbard NICHD) and are expressed as a potency relative to the present standard. The standard peptide usually blocks 50% of the LH released by GnRH at less than a ratio of 0.1 [antagonist]/1[GnRH].

The peptide described hereinabove is also used to determine effectiveness to prevent ovulation in female rats. In this test, a specified number of mature female Sprague-Dawley rats, i.e. six, each having a body weight from 225 to 250 grams, is injected with 10 micrograms of peptide in corn oil at about noon on the day of proestrous. Proestrous is the afternoon before estrous (ovulation). A separate female rat group is used as a control to which the peptide is not administered. Each of the control rat females has ovulation at estrous; of the rats treated, none of them ovulates. As a result, the peptide is considered to be significantly effective to prevent ovulation of female rats at a very low dosage, and the peptide is considered to be totally effective at a dose of about ten micrograms. Additional testing is carried out at lower dosages with the results being set forth in Table II hereinafter.

The remaining peptides Nos. 2-9 are similarly synthesized and purified. After amino acid analysis is completed, the purity is confirmed by hplc using different solvent systems. In vitro testing in similar fashion shows the peptides each to have a potency relative to the present standard antagonist as indicated. In vivo testing is carried out at varying dosages, and the results are shown in Table II.

TABLE II

| Peptide No. | in vitro Potency* | in vivo Dose (μg) | No. Ovulating |
|---|---|---|---|
| 1. | 0.44 | 10 | 0/6 |
| | | 5 | 0/8 |
| | | 2.5 | 0/10 |
| | | 1 | 0/8 |
| | | 0.5 | 2/11 |
| 2. | 1.4 | 5 | 3/6 |
| | | 1 | 0/10 |
| 3. | 0.56 | 0.5 | 2/10 |
| 4. | 0.38 | 10 | 0/8 |
| | | 5 | 0/7 |
| | | 2.5 | 0/10 |
| | | 1 | 0/4 |
| | | 0.5 | 6/6 |
| 5. | 0.20 | 5 | 4/10 |
| 6. | 0.46 | 2.5 | 9/10 |
| 7. | 0.63 | 1 | 1/10 |
| | | 0.5 | 7/10 |
| 8. | | 1 | 0/5 |
| | | 0.5 | 2/6 |
| 9. | | 1 | 0/7 |
| | | 0.5 | 0/6 |

*relative to [Ac-dehydro Pro$^1$, 4-F—D-Phe$^2$, D-Trp$^{3,6}$]-GnRH.

All peptides shown are completely effective to block GnRH-induced LH secretion in vitro at some reasonable concentration although most are slightly less potent than the present standard in vitro; however, these peptides are much more potent in vivo.

All of the peptides are considered to be effective to prevent ovulation of female mammals at very low dosages, and some selected ones are considered to be at least twice as potent as any GnRH antagonists previously known and tested.

The peptides of the invention are often administered in the form of pharmaceutically acceptable, nontoxic salts, such as acid addition salts, or of metal complexes, e.g., with zinc, barium, calcium, magnesium, aluminum or the like (which are considered as addition salts for purposes of this application), or of combinations of the two. Illustrative of such acid addition salts are hydrochloride, hydrobromide, sulphate, phosphate, nitrate, oxalate, fumarate, gluconate, tannate, maleate, acetate, citrate, benzoate, succinate, alginate, pamoate, malate, ascorbate, tartrate and the like. If the active ingredient is to be administered in tablet form, the tablet may contain a pharmaceutically-acceptable diluent which includes a binder, such as tragacanth, corn starch or gelatin; a disintegrating agent, such as alginic acid; and a lubricant, such as magnesium stearate. If administration in liquid form is desired, sweetening and/or flavoring may be used as part of the pharmaceutically-acceptable diluent, and intravenous administration in isotonic saline, phosphate buffer solutions or the like may be effected.

The pharmaceutical compositions will usually contain the peptide in conjunction with a conventional, pharmaceutically-acceptable carrier. Usually, the dosage will be from about 1 to about 100 micrograms of the peptide per kilogram of the body weight of the host when given introvenously; oral dosages will be higher. Overall, treatment of subjects with these peptides is generally carried out in the same manner as the clinical treatment using other antagonists of GnRH.

These peptides can be administered to mammals intravenously, subcutaneously, intramuscularly, orally, intranasally or intravaginally to achieve fertility inhibition and/or control and also in applications calling for reversible suppression of gonadal activity, such as for the management of precocious puberty or during radiation- or chemo-therapy. Effective dosages will vary with the form of administration and the particular species of mammal being treated. An example of one typical dosage form is a physiological saline solution containing the peptide which solution is administered to provide a dose in the range of about 0.1 to 2.5 mg/kg of body weight. Oral administration of the peptide may be given in either solid form or liquid form.

Although the invention has been described with regard to its preferred embodiments, it should be understood that changes and modifications as would be obvious to one having the ordinary skill in this art may be made without departing from the scope of the invention which is set forth in the claims which are appended thereto. For example, other substitutions known in the art which do not significantly detract from the effectiveness of the peptides may be employed in the peptides of the invention. For instance, instead of the residues specified for R$_{10}$, Gly-OCH$_3$ or Gly-OCH$_2$CH$_3$ or Gly-NHNH$_2$ or Sar-NH$_2$ (Sar=sarcosine) can be used which are considered to be equivalents thereof.

Particular features of the invention are emphasized in the claims that follow.

What is claimed is:

1. A peptide or a nontoxic salt thereof, said peptide having the formula:

X-β-D-2NAL-R$_2$-D-Trp-Ser-R$_5$-R$_6$-R$_7$-Arg-Pro-R$_{10}$ wherein X is hydrogen or an acyl group having 7 or less carbon atoms; R$_2$ is Cl-D-Phe, F-D-Phe, NO$_2$-D-Phe, Cl$_2$-D-Phe or Br-D-Phe; R$_5$ is Tyr or 2-Cl-Phe; R$_6$ is 4-NH$_2$-D-Phe or D-Arg; R$_7$ is Leu or NαMe-Leu; and R$_{10}$ is Gly-NH$_2$, NHCH$_2$CH$_3$ or D-Ala-NH$_2$.

2. A peptide in accordance with claim 1 wherein R$_2$ is 4-Cl-D-Phe or 4-F-D-Phe.

3. A peptide in accordance with claim 2 wherein R$_7$ is Leu.

4. A peptide in accordance with claim 3 wherein R$_6$ is D-Arg.

5. A peptide in accordance with claim 4 wherein R$_5$ is Tyr.

6. A peptide in accordance with claim 5 wherein X is Ac.

7. A peptide in accordance with claim 5 wherein X is Acr.

8. A peptide in accordance with claim 1 wherein X is Ac and R$_6$ is D-Arg.

9. A peptide in accordance with claim 8 wherein R$_2$ is 4-Cl-D-Phe.

10. A peptide in accordance with claim 8 wherein R$_2$ is 4-F-D-Phe.

11. A pharmaceutical composition, comprising as an active ingredient an effective amount of a peptide as defined in claim 1 for regulating the secretion of gonadatropins, in association with a major amount of a nontoxic pharmaceutically-acceptable diluent.

12. A method for regulating the secretion of gonadotropins in mammals, which method comprises administering an effective amount of a peptide having the formula:

X-β-D-2NAL-R$_2$-D-Trp-Ser-R$_5$-R$_6$-R$_7$-Arg-Pro-R$_{10}$ wherein X is hydrogen or an acyl group having 7 or less carbon atoms; R$_2$ is Cl-D-Phe, F-D-Phe, NO$_2$-D-Phe, Cl$_2$-D-Phe or Br-D-Phe; R$_5$ is Tyr or 2-Cl-Phe; R$_6$ is 4-NH$_2$-D-Phe or D-Arg; R$_7$ is Leu or NαMe-Leu; and R$_{10}$ is Gly-NH$_2$, NHCH$_2$CH$_3$ or D-Ala-NH$_2$.

13. A method in accordance with claim 12 wherein said peptide is administered so as to provide a dose in the range of between about 0.1 and 2.5 mg/kg of body weight.

14. A peptide or a nontoxic salt thereof, said peptide having the formula:

X-β-D-2NAL-R$_2$-D-Trp-Ser-R$_5$-D-Arg-R$_7$-Arg-Pro-R$_{10}$ wherein X is hydrogen or Ac or Acr; R$_2$ is 4Cl-D-Phe or 4F-D-Phe; R$_5$ is Tyr or 2-Cl-Phe; R$_7$ is Leu or NαMe-Leu; and R$_{10}$ is Gly-NH$_2$, NHCH$_2$CH$_3$ or D-ala-NH$_2$.

15. A peptide in accordance with claim 14 wherein R$_5$ is 2-Cl-Phe and R$_{10}$ is Gly-NH$_2$.

16. A peptide in accordance with claim 15 wherein X is Ac, R$_2$ is 4F-D-Phe and R$_7$ is Leu.

17. A peptide in accordance with claim 14 wherein R$_2$ is 4F-D-Phe and R$_5$ is Tyr.

18. A peptide in accordance with claim 17 wherein X is Ac and R$_{10}$ is Gly-NH$_2$.

19. A peptide in accordance with claim 14 wherein R$_2$ is 4Cl-D-Phe and R$_5$ is Tyr.

20. A peptide in accordance with claim 19 wherein X is Ac, R$_7$ is Leu and R$_{10}$ is NHCH$_2$CH$_3$.

* * * * *